United States Patent
Kaneko et al.

(10) Patent No.: US 9,005,336 B2
(45) Date of Patent: Apr. 14, 2015

(54) MONOTERPENE COMPONENT-RICH ESSENTIAL OIL, METHOD FOR PRODUCING SAME AND METHOD FOR REMEDIATING ENVIRONMENTAL POLLUTANTS USING THE ESSENTIAL OIL

(75) Inventors: Toshihiko Kaneko, Tokyo (JP); Yuichi Tanaka, Tokyo (JP); Tatsuro Ohira, Ibaraki (JP); Naoyuki Matsui, Ibaraki (JP)

(73) Assignee: S.T. Corporation, Tokyo (JP)

( * ) Notice: Subject to any disclaimer, the term of this patent is extended or adjusted under 35 U.S.C. 154(b) by 782 days.

(21) Appl. No.: 13/203,591

(22) PCT Filed: Feb. 26, 2010

(86) PCT No.: PCT/JP2010/053068
§ 371 (c)(1),
(2), (4) Date: Aug. 26, 2011

(87) PCT Pub. No.: WO2010/098440
PCT Pub. Date: Sep. 2, 2010

(65) Prior Publication Data
US 2012/0012002 A1 Jan. 19, 2012

(30) Foreign Application Priority Data
Feb. 26, 2009 (JP) ................... 2009-043709

(51) Int. Cl.
*B01D 3/34* (2006.01)
*C11B 9/02* (2006.01)
(Continued)

(52) U.S. Cl.
CPC . *C11B 9/027* (2013.01); *B01D 3/38* (2013.01); *A61L 9/013* (2013.01); *B01D 53/1493* (2013.01); *B01D 53/46* (2013.01); *B01D 53/77* (2013.01); *B01D 2251/21* (2013.01);
(Continued)

(58) Field of Classification Search
None
See application file for complete search history.

(56) References Cited

U.S. PATENT DOCUMENTS 5,338,557 A * 8/1994 Pare .............................. 426/241
6,538,164 B1 * 3/2003 Gallagher et al. ............ 568/871
(Continued)

FOREIGN PATENT DOCUMENTS

FR 2 717 492 A1 9/1995
FR 2717492 A1 * 9/1995
(Continued)

OTHER PUBLICATIONS

International Search Report dated Sep. 13, 2011.*
(Continued)

*Primary Examiner* — Duane Smith
*Assistant Examiner* — Phillip Shao
(74) *Attorney, Agent, or Firm* — Oblon, McClelland, Maier & Neustadt, L.L.P.

(57) ABSTRACT

To develop a means for effectively utilize terpene compounds contained in tree leaves, whereby branches and leaves cut in tree thinning and pruning can be effectively utilized as a resource. For this purpose, provided are a monoterpene component-rich essential oil containing 90% or more of monoterpene components; a method for producing the monoterpene component-rich essential oil which includes subjecting coniferous leaves to microwave steam distillation and collecting a distillate thus obtained; and a method for removing environmental pollutants which includes bringing the monoterpene component-rich essential oil into contact with atmosphere containing the environmental pollutants.

1 Claim, 3 Drawing Sheets

(51) Int. Cl.
  *B01D 53/14* (2006.01)
  *B01D 53/46* (2006.01)
  *B01D 3/38* (2006.01)
  *A61L 9/013* (2006.01)
  *B01D 53/77* (2006.01)

(52) U.S. Cl.
  CPC .... *B01D 2257/302* (2013.01); *B01D 2257/404* (2013.01); *B01D 2257/70* (2013.01)

(56) References Cited

U.S. PATENT DOCUMENTS

| | | |
|---|---|---|
| 7,001,629 B1 | 2/2006 | Mengal et al. |
| 2002/0086906 A1 | 7/2002 | Weidner et al. |
| 2003/0157204 A1 | 8/2003 | Weidner et al. |

FOREIGN PATENT DOCUMENTS

| | | | |
|---|---|---|---|
| GB | 765752 A | | 1/1957 |
| GB | 2 374 296 A | | 10/2002 |
| GB | 2374296 A | * | 10/2002 |
| JP | 6 327934 | | 11/1994 |
| JP | 8 512337 | | 12/1996 |
| JP | 11290652 A | * | 10/1999 |
| JP | 2000 210526 | | 8/2000 |
| JP | 2000210526 A | * | 8/2000 |
| JP | 3498133 | | 12/2003 |
| WO | WO 99/53935 A1 | | 10/1999 |

OTHER PUBLICATIONS

English Translation of JP 2000210526 A, accessed Jun. 11, 2014.*
English Translation of FR 2717492 A1, accessed Jun. 11, 2014.*
English Translation of JP 11290652 A, accessed Jun. 11, 2014.*
English Translation of GB 2374296 A, accessed Jun. 11, 2014.*
International Search Report Issued Mar. 23, 2010 in PCT/JP10/053068 filed Feb. 26, 2010.
Extended European Search Report issued Aug. 9, 2012 in Patent Application No. 10746319.2.
William S. Schlotzhauer, et al., "Volatile Constituents from the Flowers of Japanese Honeysuckle (*Lonicera japonica*)", Journal of Agricultural and Food Chemistry, XP001018426, vol. 44, No. 1, Jan. 1, 1996, pp. 206-209.

* cited by examiner

MONOTERPENE COMPONENT-RICH ESSENTIAL OIL, METHOD FOR PRODUCING SAME AND METHOD FOR REMEDIATING ENVIRONMENTAL POLLUTANTS USING THE ESSENTIAL OIL

TECHNICAL FIELD

This invention relates to a monoterpene component-rich essential oil which contains monoterpene compounds at an extremely high concentration, a method for producing the same with the use of coniferous leaves as the starting material, and a method for remediating environmental pollutants using the essential oil.

BACKGROUND ART

Because of difficulties in finding forestry successors and falling in timber price, forest management has become more and more difficult, which brings about a serious problem of deserted forests. Although tree thinning and pruning are main procedures in forest management, timbers from thinning and branches and leaves cut off thereby are not only economically valueless but require an additional cost. Therefore, it is no surprise that these management procedures are neglected.

Under these circumstances, attempts have been made in these years to process wood materials obtained by tree thinning and so on to thereby provide useful resources. For example, timbers from thinning are chipped, cooked and then used as animal feeds.

However, the aforesaid method requires large equipment for chipping and cooking and, therefore, is not easily available anywhere. Setting timbers aside, no method has been known so far for effectively utilizing branches and leaves.

It is known that smokes containing various chemicals such as nitrogen oxides (NOx) and sulfur oxides (SOx) are discharged from boilers operated in power stations and plants and refuse incinerator sites. It is also known that automobile exhausts contain various chemicals harmful to humans, in particular, NOx and SOx.

These NOx and SOx are not only harmful to humans but also cause acid rainfall. Furthermore, photochemical reactions induced by solar light in the coexistence of NOx and non-methane hydrocarbons cause photochemical smog. Photochemical smog is a phenomenon caused by hydrocarbons and NOx in atmosphere which absorb ultraviolet light and undergo photochemical reactions to form harmful photochemical oxidants and the like. However, the delay in countermeasures against NOx, in particular, NOx discharged from mobile sources such as automobiles has brought about serious problems.

It is also known that various volatile organic solvents are used in interior materials such as wall papers and these VOCs (volatile organic compounds) volatilize indoors. That is, adhesives are widely used in architectural materials and furniture employed for building houses and constructing internal equipments. It is known that, as these adhesives, urea resin-based adhesives, melamine/urea co-condensation resin-based adhesives, phenolic resin-based adhesives and the like are frequently employed from the stand points of performance, cost and convenience. These adhesives, which contain formaldehyde employed as one of starting materials and therefore also called formaldehyde-type adhesives, release formaldehyde into atmosphere.

For example, a urea resin-based adhesive as described above cures through the formation of methylol group by an addition reaction of formaldehyde followed by the formation of methylene bond and dimethylene-ether bond by condensation. Formaldehyde is released not only in the course of the curing as described above but also from the cured adhesive. Namely, deformaldehyde accompanies the progress of the decomposition of the methylol group and the condensation of the dimethylene-ether bond to the methylene bond. Accordingly, formaldehyde is continuously released from the cured urea resin-based adhesive over a long period of time. The same phenomenon is observed in many other adhesives excluding phenolic resins which scarcely release formaldehyde.

Concerning methods for removing these environmental pollutants such as NOx, SOx and formaldehyde as described above, methods for removing NOx by passing an NOx-containing material through a solution of an absorbent such as a carboxylic acid or an alkali or passing the same through a specific machine have been developed. However, these methods require troublesome procedures and high cost. As another method, Patent Document 1 discloses an agent for removing harmful chemicals which contains, as the active ingredient, an aqueous solution containing plant essential oil containing an essential oil obtained by steam-distilling a plant, a water-soluble fraction obtained in the steam distillation and water. Patent Document 2 discloses a method for removing NOx, which includes gasifying a terpene compound having conjugated double bond such as α-terpinene, myrcene or alloocimen and dispersing the same into the air so as to include NOx contained in the air into the terpene compound.

Concerning formaldehyde, the present inventors disclose a method for capturing formaldehyde, containing: (a) a step for sucking formaldehyde-containing air into a first container and bringing the air into contact with complex volatile aroma components, having been extracted from tree leaves, in the container to thereby capture formaldehyde; (b) the step for removing ozone from the air having been treated in the above step; and (c) a step for bringing the air, from which ozone has been removed, into contact with silica gel coated with 2,4-dinitrophenylhydrazine to thereby further capture formaldehyde in the gas (Patent Document 3).

Although distillate components obtained by steam distillation are used in all of the methods of Patent Documents 1, 2 and 3, such substances obtained by steam distillation contain a large amount of irritating smell-generating components such as phenol. Therefore, these substances cannot be dispersed directly into atmosphere. Before dispersing into atmosphere, these substances should be purified to remove the aforesaid irritating components. Such purification causes an additional cost and, therefore, brings about an economical problem.

It is known that plant leaves contain terpene compounds. Application of these terpene compounds to the final removal of environmental pollutants, if possible, contributes to the effective utilization of branches and leaves obtained by tree thinning and pruning as a resource. However, no means therefor has been known so far.

RELATED ART REFERENCES

Patent Documents

[Patent Document 1] Japanese Patent Laid-Open No. 210526/2000
[Patent Document 2] Japanese Patent Laid-Open No. 327934/1994
[Patent Document 3] Japanese Patent No. 3498133

SUMMARY OF THE INVENTION

Problems that the Invention is to Solve

An object of the present invention is to develop a means for efficiently separating terpene compounds contained in tree leaves and using the same particularly for removing environmental pollutants.

Means for Solving the Problems

The present inventors conducted intensive studies on the effective utilization of branches and leaves obtained by tree thinning and pruning that have been scarcely utilized so far. As a result, they found that an essential oil fraction containing an extremely large amount of specific terpene compounds can be obtained by distilling the aforesaid materials under specific conditions and environmental pollutants can be very efficiently removed by using the essential oil fraction. The present invention has been completed based on these findings.

Specifically, the present invention relates to a monoterpene component-rich essential oil containing 90% or more of monoterpene components.

Further, the present invention relates to a method for producing the aforesaid monoterpene component-rich essential oil, which includes distilling coniferous leaves by heating under reduced pressure and collecting an oily fraction thus obtained as a distillate.

Further, the present invention relates to a method for removing environmental pollutants, which includes bringing the aforesaid monoterpene component-rich essential oil into contact with atmosphere containing the environmental pollutants.

Advantage of the Invention

The monoterpene component-rich essential oil according to the present invention is obtained from branches and leaves obtained by tree thinning and pruning and contains 90% or more of monoterpene components together with extremely small amounts of sesquiterpene components and diterpene components.

This essential oil enables effective removal of environmental pollutants such as harmful oxides including NOx and SOx and formalin. Therefore, it is usable as an agent for removing these substances. It is also useful as a less expensive starting material of terpene-based perfume components.

The device to be used in the method according to the present invention has a small size, compared with steam distillation devices commonly employed, and is available with the use of a power source for commercial purposes. Thus, it can be installed in a logging area and operated at a low cost.

MODE FOR CARRYING OUT THE INVENTION

Figure 1:
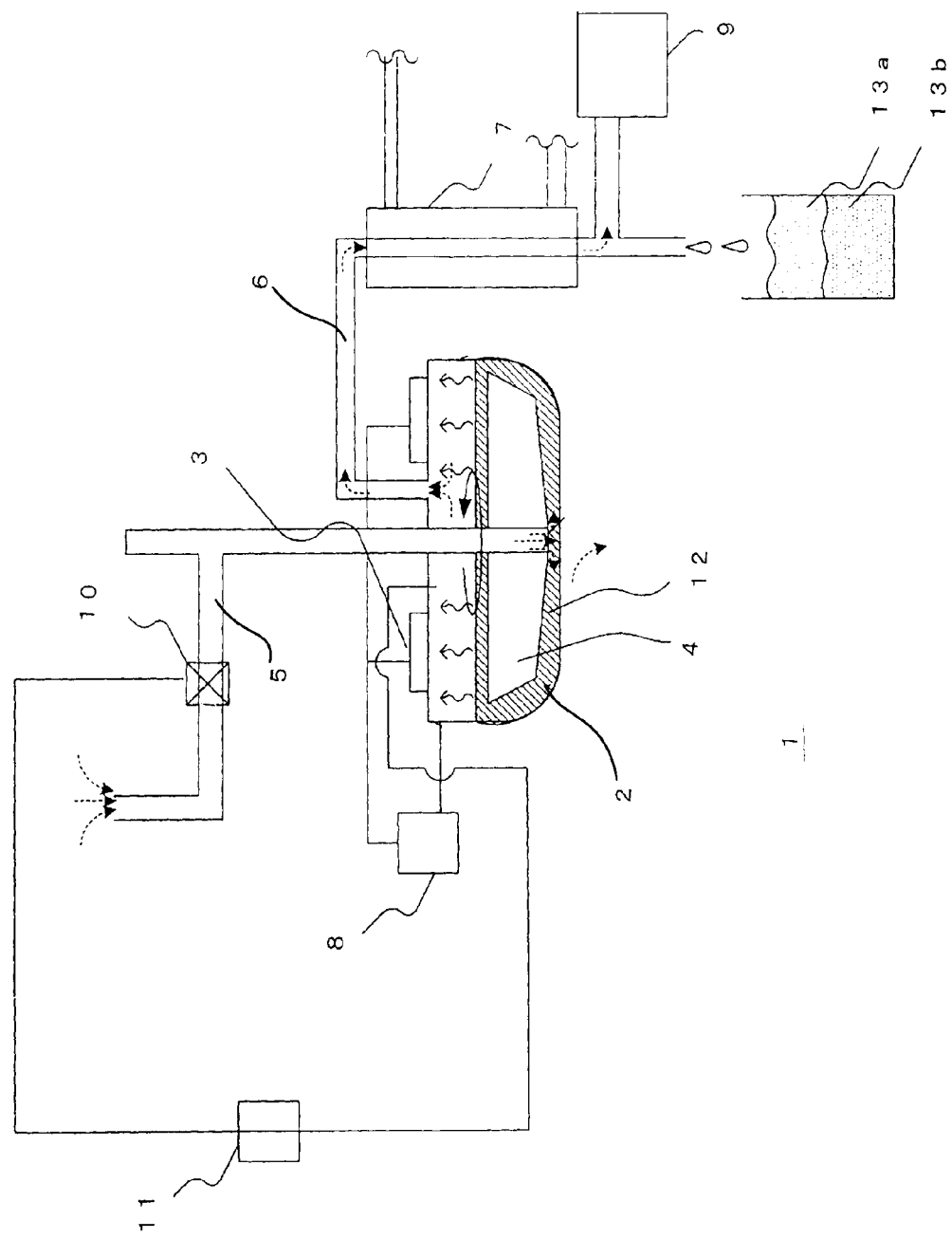
FIG. 1 is a model view which shows the constitution of a microwave vacuum steam distillation device to be used in the method of the present invention.

The monoterpene component-rich essential oil according to the present invention, which contains 90% or more of monoterpene components, can be obtained by distilling coniferous leaves by heating under reduced pressure (hereinafter referred to as "vacuum steam distillation method") and then collecting an oily extraction fraction thus obtained, without the need for further purification.

The coniferous leaves employed as the starting material are not specifically restricted. Examples include leaves of Cupressaceae *Chamaecyparis* trees such as *Chamaecyparis obtusa* Chamaecyparis, *Chamaecyparis obtusa* var. *formosana*, *Chamaecyparis nootkatensis* (D. Don) Spach, *Chamaecyparis pisifera* Fillifera Aurea, *Chamaecyparis lawsoniana*, *Chamaecyparis obtusa* Breviramea, *Chamaecyparis obtusa* cv. *Filicoides Aurea*, *Chamaecyparis pisifera* cv. *Nana aurea*, *Chamaecyparis obutusa* Endl. var. *pendula* Mast, *Chamaecyparis pisifera* Filifera, *Chamaeciyparis pisifera* Filifera Aurea, *Chamaecyparis pisifera* Plumosa, *Chamaecyparis pisifera* (Sieb. et Zucc.) Endl. cv. Plumosaaurea and *Chamaecyparis pisifera* var. *squarrosa*; Cupressaceae *Thuja* trees such as *Thuja occidentalis* and *Thuja standishii*; Cupressaceae *Thujopsis* trees such as *Thujopsis dolabrata*, *Thujopsis dolabrata*, *Thujopsis dolabrata* var. *hondae* and *Thujopsis dolabrata* var. *hondae f. uchimappeana*; Cupressaceae *Juniperus* trees such as *Juniperus chinensis* var. *procumbens*, *Juniperus rigida*, *Juniperus virginiana* and *Juniperus taxifolia* var. *lutchuensis* (*Juniperus taxifolia* var. *lutchuensis*); Cupressaceae *Cryptomeria* trees such as *Cryptomeria japonica*, *Cryptomeria japonica* var. *radicans*, *Cryptomeria japonica* v. *araucarioides* Henk et Hochst, *Cryptomeria japonica* Yoresugi, *Cryptomeria japonica* (L. f.) D. Don cv. Aurea, *Cryptomeria japonica* Cristata and *Cryptomeria japonica* Viridis; Pinaceae *Abies* trees such as *Abies sachalinensis*, *Abies firma*, *Abies homolepis*, *Abies veitchii*, *Abies mariesii*, *Abies veitchii* Lindl, *Abies balsamea* (Linnaeus) Miller, *Abies homolepis* var. *umbellata*, *Abies alba*, *Abies amabilis*, *Abies sachalinensis* Masters var. *mayriana* Miyabe et Kudo, *Abies magmifica*, *Abies grandis* and *Abies procera*; Pinaceae *Cedrus* trees such as *Cedrus deodara*; Pinaceae *Picea* trees such as *Picea glehnii* Masters and *Picea jezoensis* var. *hondoensis*; Pinaceae *Pinus* trees such as *Pinus densiflora* Sieb. et Zucc, *Pinus palustris* Mill, *Pinus strobes* Linnaeus and *Pinus pumila*; Pinaceae *Larix* trees such as *Larix kaempferi*; Pinaceae *Tsuga* trees such as *Tsuga sieboldii*; Sciadopityaceae *Sciadopitys* trees such as *Sciadopitys verticillata*; and Taxaceae *Torreya* trees such as *Torreya nucifera*. Although these leaves may be used on their own in the state of timbers from thinning and branches and leaves obtained by tree thinning and pruning, it is preferred to grind or crush them by a grinder or a crusher before using.

In the vacuum steam distillation method to be used for obtaining the monoterpene component-rich essential oil from these coniferous leaves, heating may be directly conducted with the use of a heater. However, it is preferred to employ a method including irradiating the starting material (e.g., the coniferous leaves) with microwave and thus extracting the essential oil exclusively with water, that is inherently contained in the starting material, by taking advantage of the properties of microwave whereby water molecules can be directly heated (hereinafter referred to as "microwave vacuum steam distillation method").

A microwave vacuum steam distillation device is required for conducting the microwave vacuum steam distillation method. FIG. 1 roughly shows an embodiment of this device. In FIG. 1, 1 represents a microwave distillation device; 2 represents a distillation tank; 3 represents a microwave heater; 4 represents a stirring blade; 5 represents a gas stream inlet tube; 6 represents a distillate outlet tube; 7 represents a condenser; 8 represents a heating controller; 9 represents a vacuum pump; 10 represents a pressure controlling valve; 11 represents a pressure controller; 12 represents a target material to be distilled; and 13 represents an extract.

In the device 1, a starting material 12 to be distilled (coniferous leaves in the present invention) is supplied into the distillation tank 2. Under stirring with the stirring blade 4, the starting material is heated by irradiating with microwave from the microwave heater 3 which is provided on the upper surface of the distillation tank 2. The distillation tank 2 is connected to the gas stream tube 5 and the distillate outlet tube 6. The gas stream inlet tube 5 is provided for introducing an inert gas such as air or nitrogen gas into the reaction distillation tank 2. The gas stream is introduced from the lower part of the distillation tank 2. The distillate outlet tube 6 is provided for discharging outside the distillate, which has been obtained from the starting material, from the upper part of the distillation tank 2.

The temperature and pressure in the distillation tank 2 can be measured with a temperature sensor and a pressure sensor (both not shown in the drawing) attached to the reaction tank 2. The temperature and pressure are controlled respectively with the heating controller 8 and the pressure controller 11 through the pressure controlling valve 10.

The gaseous distillate flowing out from the distillation tank 2 through the distillate outlet tube 6 is liquefied by the condenser 7 and obtained as the extract 13. This extract 13 consists of an aqueous fraction 13b and an oily fraction 13a. The oily fraction 13a is to be used as the essential oil.

In the method according to the present invention, the pressure in the distillation tank 2 may be controlled to 10 to 95 kPa, preferably 20 to 80 kPa and still preferably about 30 to 60 kPa. In this step, the steam temperature is 40 to 100° C. When the pressure is less than 10 kPa, the yield of the essential oil becomes very low. When the pressure is more than 95 kPa, the monoterpene content is lowered. The distillation time may be adjusted to about 0.2 to 8 hours, preferably about 0.4 to 6 hours. When the distillation time is less than 0.2 hour, the distillation cannot be sufficiently carried out. Even though the distillation is continued more than 8 hours, the yield cannot be increased any more and, moreover, the content of impurities such as sesquiterpenes and diterpenes is increased.

Although air is usable as the gas to be introduced into the distillation tank 2, it is preferred to use an inert gas such as nitrogen gas, helium gas or argon gas. The flow rate of the gas may be 0.001 to 0.1 time as much as the capacity of the distillation tank 2 per minute.

The thus obtained monoterpene component-rich essential oil according to the present invention is characterized by containing 90% or more of monoterpene components. In contrast thereto, an essential oil obtained by the conventional steam distillation contains a considerably large amount of sesquiterpenes and diterpenes, as will be shown in Examples. Thus, it is clarified that essential oils having different terpene compositions can be obtained, even from the same starting material, by using different distillation means.

The monoterpene component-rich essential oil according to the present invention can be advantageously used in removing environmental pollutants. Namely, it can effectively remove harmful oxides such as NOx and SOx, formaldehyde and so on and, therefore, is usable as an environmental pollutant-removing agent. That is, NOx and SOx in atmosphere can be removed by, for example, a method which includes impregnating a filter made of a paper (pulp), a nonwoven fabric, a resin sheet, a wood sheet, a wood flour, resin beads or the like with the monoterpene component-rich essential oil and then passing air containing NOx and SOx through the filter to thereby bring the air into contact with the active ingredients. Alternatively, NOx and SOx in atmosphere can be removed by a method which includes bubbling air containing NOx and SOx into a removing agent containing the monoterpene component-rich essential oil to thereby bring the air into contact with the active ingredients.

Another examples of the method for bringing the monoterpene component-rich essential oil according to the present invention into contact with atmosphere and thus removing environmental pollutants in atmosphere include: a method of volatilizing an environmental pollutant-removing agent containing the monoterpene component-rich essential oil according to the invention directly or by using an appropriate volatilization device; a method of volatilizing the same in an atomized state by using an atomizer such as a pump spray, an aerosol, an ultrasonic transducer, a pressurized liquid spray or a pressurized air atomizing spray device, and so on. By these methods, environmental pollutants can be removed from daily living space.

As discussed above, the monoterpene component-rich essential oil according to the present invention contains monoterpene components, which are all components of perfumes and harmless to humans, at high concentration. When contacted with atmosphere in living space or volatilized thereinto, therefore, the monoterpene component-rich essential oil according to the invention neither causes unpleasantness nor exerts any undesirable effect on humans, animals or plants.

Since the monoterpene component-rich essential oil according to the present invention contains monoterpene components in an amount of 90% or more, it is also usable as a starting material for the individual monoterpenes.

EXAMPLES

To further illustrate the present invention in greater detail, the following Examples will be given. However, it is to be understood that the invention is not restricted to these Examples.

Example 1

By using *Cryptomeria japonica* leaves as the staring material, a *Cryptomeria japonica* essential oil was obtained in the following manner. About 50 kg of *Cryptomeria japonica* leaves having been ground with a crush type grinder (manufactured by KYB Seisakusho) were fed into the distillation tank of the microwave vacuum steam distillation device shown in FIG. 1. Under stirring and maintaining the pressure in the distillation tank at a reduced pressure level of about 20 kPa (steam temperature: about 67° C.), the starting material was distilled by irradiating with microwave for 1 hour. Thus, 180 mL of an essential oil was obtained and the yield of the essential oil relative to the starting material employed was 0.34%.

The terpene composition of the obtained essential oil was measured with a gas chromatograph/mass spectrometer. Table 1 shows the results.

Comparative Example 1

By using the same *Cryptomeria japonica* leaves as in Example 1, steam distillation was conducted in the following manner to give a *Cryptomeria japonica* oil. About 101 g of the *Cryptomeria japonica* leaves having been ground with a crush type grinder (manufactured by KYB Seisakusho) were fed into a Pyrex® glass flask. After adding 5 to 8 times as much water, the flask was heated in a hot water bath at 90 to 100° C. and thus the contents were boiled. Before heating, water was added to a standard level in an essential oil-collecting tube.

After boiling for 6 hours to distill the material, 0.8 mL of an essential oil was obtained. The yield of the essential oil relative to the starting material employed was 0.79% The terpene composition of the obtained essential oil was measured as in Example 1. Table 1 shows the results.

TABLE 1

| Terpene contained | *C. japonica* leaf essential oil of Example 1 | *C. japonica* leaf essential oil of Comparative Example 1 |
|---|---|---|
| (Monoterpene) | | |
| α-pinene | 34 | 8 |
| sabinene | 29 | 4 |
| limonene | 14 | 0 |
| β-myrcene | 6 | 1 |
| δ-3-carene | 5 | 5 |
| β-pinene | 2 | 0 |
| α-thujene | 2 | 0 |
| γ-terpinene | 1 | 1 |
| α-terpinolene | 1 | 1 |
| terpinen-4-ol | 1 | 2 |
| α-terpinene | 0 | 1 |
| <Total of monoterpenes> | 94 | 23 |
| (Sesquiterpene) | | |
| β-cubebene | 2 | 4 |
| α-muurolene | 0 | 0 |
| γ-cadinene | 0 | 0 |
| δ-cadinene | 1 | 3 |
| α-elemol | 1 | 16 |
| elixene | 0 | 0 |
| γ-muurolene | 0 | 1 |
| α-glucuene | 0 | 1 |
| γ-eudesmol | 0 | 9 |
| copaene | 0 | 1 |
| γ-selinene | 0 | 15 |
| (Diterpene) | | |
| kau-16-ene | 2 | 26 |
| isopimeradiene | 0 | 1 |
| <Total of components other than monoterpenes> | 6 | 77 |
| Total | 100 | 100 |

(Figures in the table are contents expressed in mol %.)

The results show that, even by using the same coniferous leaves (*Cryptomeria japonica* leaves), the composition of the essential oil produced by using the microwave vacuum steam distillation device differs substantially from the composition of the essential oil produced by using commonly employed steam distillation.

Example 2

An essential oil was obtained in the same manner as in Example 1 except that the *Cryptomeria japonica* leaves were replaced with *Abies sachalinensis* leaves. Table 2 shows the terpene composition of the obtained essential oil.

TABLE 2

| Terpene contained (Monoterpene) | *A. sachalinensis* leaf essential oil of Example 2 |
|---|---|
| α-pinene | 24 |
| camphene | 22 |
| β-phellandrene | 18 |
| bornyl acetate | 11 |
| β-pinene | 10 |
| limonene | 6 |
| β-myrcene | 5 |
| tricyclene | 3 |
| δ-3-carene | 1 |
| α-terpinolene | 1 |
| <Total of monoterpenes> | 100 |
| <Total of components other than monoterpenes> | 0 |
| Total | 100 |

(Figures in the table are contents expressed in mol %.)

Example 3

An essential oil was obtained in the same manner as in Example 1 except that the *Cryptomeria japonica* leaves were replaced with *Chamaecyparis obtusa Chamaecyparis* leaves. Table 3 shows the terpene composition of the obtained essential oil.

TABLE 3

| Terpene contained | *C. obtusa Chamaecyparis* leaf essential oil of Example 3 |
|---|---|
| (Monoterpene) | |
| sabinene | 48 |
| limonene | 10 |
| α-terpinyl acetate | 9 |
| β-phellandrene | 9 |
| bornyl acetate | 7 |
| γ-terpinene | 5 |
| α-pinene | 4 |
| α-terpinolene | 2 |
| α-thujene | 1 |
| <Total of monoterpenes> | 94 |
| (Sesquiterpene) | |
| cis-thujopsonene | 4 |
| cis-muurola-4(14), 5-diene | 1 |
| germacrene D | 2 |
| <Total of components other than monoterpenes> | 7 |
| Total | 100 |

(Figures in the table are contents expressed in mol %.)

Examples 1 to 3 prove that each of the essential oils obtained by the microwave vacuum steam distillation device shows an extremely high monoterpene content.

Test Example 1

(1) Test on nitrogen dioxide concentration-reducing effect: About 0.1 g of paper rag was packed in a glass tube having an inner diameter of 5 mm and then impregnated with each of the removal agents according to the present invention in the amount listed in Table 4. One end of the glass tube was connected to a Tedlar bag containing 8.5 ppm of nitrogen dioxide and the other end thereof was connected to a nitrogen dioxide gas detection tube (manufactured by Gastech). The other end of the gas detection tube was connected to a suction syringe.

In the aforesaid state, nitrogen dioxide in the Tedlar bag was sucked with the sucking syringe and the concentration of nitrogen dioxide having not removed in the glass tube was measured by the gas detection tube. As a blank, paper rag not impregnated with the removal agent was used. Thus, the nitrogen dioxide-removing effect was determined in accordance with the following formula. Table 4 shows the results.

Removal ratio (%)=$(B-A)/B \times 100$

A: nitrogen dioxide concentration after passing through removal agent

B: nitrogen dioxide concentration after passing through blank (2) Test on Sulfur Dioxide Concentration-Reducing Effect The procedure of (1) was followed except that 8.5 ppm of nitrogen dioxide was replaced with 4.2 ppm of sulfur dioxide and a sulfur dioxide detection tube (manufactured by Gastech) was used as a detection tube. By using the aforesaid formula, wherein the nitrogen dioxide concentrations were substituted by sulfur dioxide concentrations, the sulfur dioxide-removing effect was determined. Table 4 shows the results.

TABLE 4

| Sample | Amount (μL) | Removal ratio (%) NO$_2$ | Removal ratio (%) SO$_2$ |
|---|---|---|---|
| C. japonica leaf essential oil | 20 | 100 | 87.4 |
| A. sachalinensis leaf essential oil | 20 | 72.5 | 56.9 |
| C. obtusa Chamaecyparis leaf essential oil | 20 | 100 | 73.2 |

Example 4

Test on Formaldehyde Concentration-Reducing Effect

Each of the essential oils obtained in Examples 1 to 3 was adjusted to a concentration of 5% with n-hexane and a 3 ml portion thereof was put into an impinger. One opening of the impinger was connected to a Tedlar bag containing formaldehyde (0.95 ppm) and the other opening was connected to a DNPH cartridge for detecting aldehyde. After sucking at 100 mL/min for 30 minutes, the adsorbed components were eluted from the DNPH cartridge by a definite method and subjected to HPLC to determine the formaldehyde concentration. The formaldehyde-removing ratio was determined in accordance with the following formula using the formaldehyde concentration measured in the case of passing n-hexane alone as a control. Table 5 shows the results.

Removal ratio (%)=$(B-A)/B \times 100$

A: formaldehyde concentration after passing through sample

B: formaldehyde concentration after passing through control

TABLE 5

| Sample | Removal ratio (%) |
|---|---|
| C. japonica leaf essential oil | 100 |
| A. sachalinensis leaf essential oil | 86 |
| C. obtusa Chamaecyparis leaf essential oil | 100 |

Example 5

By using the essential oils obtained in Examples 1 to 3, the nitrogen dioxide-removing effects in gaseous state were examined by the following method.

1 L of air packed in a compressed gas cylinder and 50 μL of an essential oil according to the present invention were injected into a 1 L Tedlar bag. After allowing to stand in a thermostat at 40° C. for 10 minutes or longer, a headspace of the essential oil (a gas according to the invention) was obtained.

Next, the whole amount of the gas according to the invention was injected into a 20 L Tedlar bag which was then filled up with clean air to a volume of 20 L. Then, nitrogen dioxide (6.2 ppm) was injected thereinto and the nitrogen dioxide concentration was measured with a detection tube 3 minutes and 30 minutes after the injection. Thus, the nitrogen dioxide removal ratio was determined. Table 6 shows the results.

TABLE 6

| | NO$_2$ removal ratio (%) | |
|---|---|---|
| Sample | After 3 min | After 30 min |
| C. japonica leaf essential oil | 52 | 76 |
| C. obtusa Chamaecyparis leaf essential oil | 52 | 76 |
| A. sachalinensis leaf essential oil | 35 | 68 |

Example 6

Figure 4:
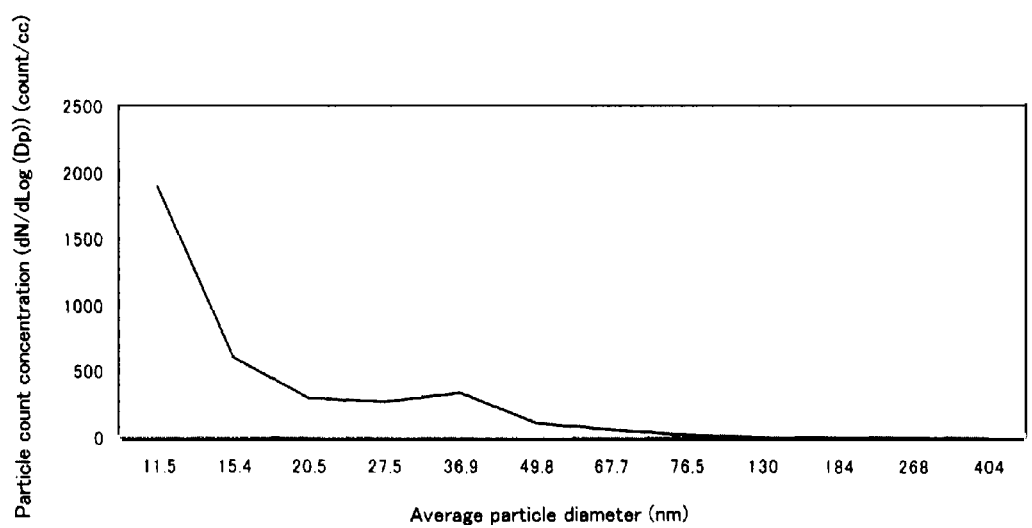
FIG. 4 is a graph which shows the distribution of nitrogen dioxide particle diameter.
Figure 5:
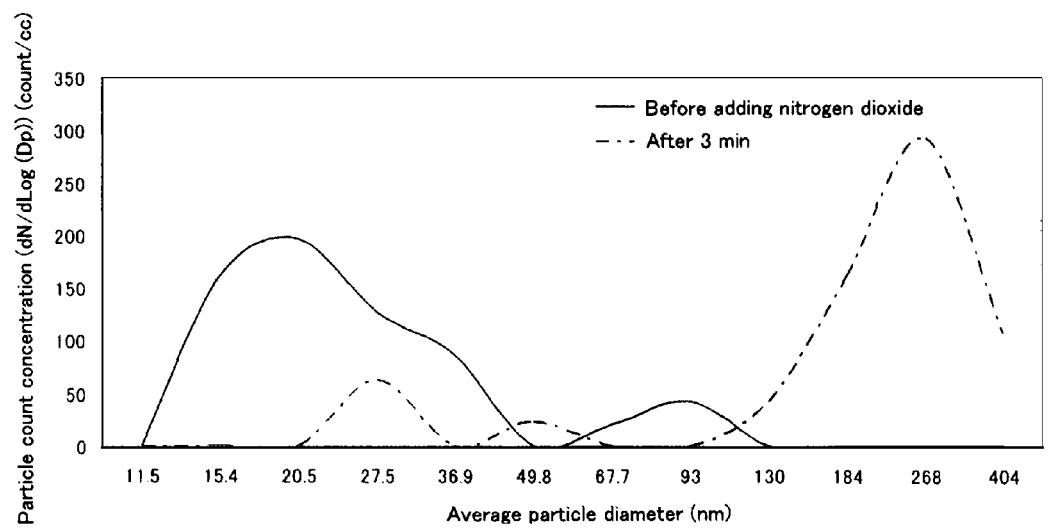
FIG. 5 is a graph which shows the particle diameter distribution in a *Cryptomeria japonica* leaf essential oil head space and the particle diameter distribution after adding nitrogen dioxide to the *Cryptomeria japonica* leaf essential oil head space.

Formation of Particles by Reaction Between Nitrogen Dioxide and Essential Oil Components 1 L of air packed in a compressed gas cylinder and 50 μl of the *Cryptomeria japonica* leaf essential oil obtained in Example 1 were injected into a 1 L Tedlar bag. After allowing to stand at 40° C. for 10 minutes, the whole amount of the headspace of the *Cryptomeria japonica* leaf essential oil having volatilized was injected into a 20 L Tedlar bag which was then filled up with clean air to a volume of 20 L. Then, nitrogen dioxide (6.2 ppm) was injected thereinto. Three minutes after the injection, the particle diameters were measured with a particle counter (Wide-Range Particle Spectrometer) MODEL 1000XP (manufactured by MSP, USA). As blanks, samples prepared by injecting nitrogen dioxide alone and the *Cryptomeria japonica* leaf essential oil alone (before adding nitrogen dioxide) were respectively subjected to the same measurement. FIGS. 4 and 5 show the results.

In these results, no larger particle was observed 3 minutes after the injection in the samples prepared by injecting nitrogen dioxide alone and the *Cryptomeria japonica* leaf essential oil according to the present invention alone. In contrast thereto, particles with large diameter were formed in the sample prepared by injecting nitrogen dioxide to the *Cryptomeria japonica* leaf essential oil according to the invention. Therefore, it is considered that, when mixed with nitrogen dioxide, the *Cryptomeria japonica* leaf essential oil in a gaseous state according to the invention quickly formed particles with large diameter and thus suppressed the reactivity of nitrogen dioxide.

Example 7

Test for Confirming Inhibition of Oxidation by Nitrogen Dioxide (1)

From the ratio of inhibiting linoleic acid peroxide formation, the effect of the essential oil according to the present invention of inhibiting the oxidation by nitrogen dioxide was examined in the following manner.

A 0.1 mL portion of a chloroform solution containing 10% of linoleic acid was dropped onto a Petri dish having a diameter of about 9 cm. Then, the solvent was volatilized under gently rotating the dish so as to uniformly coated the bottom face of the Petri dish with linoleic acid. A corner of a 10 L Tedlar bag was cut off to form an opening. The Petri dish was put into the bag and then the opening was heat-sealed.

Separately, 50 µL of the *Cryptomeria japonica* leaf essential oil, i.e., the monoterpene component-rich essential oil according to the present invention, was injected into a 1 L Tedlar bag which was then filled up with air packed in a compressed gas cylinder and allowed to stand in a thermostat at 40° C. for 10 minutes to give *Cryptomeria japonica* leaf essential oil headspace-containing Tedlar bag. 1 L of the *Cryptomeria japonica* leaf essential oil headspace was injected into the bag containing the linoleic acid-coated Petri dish. After adding 150 mL of nitrogen dioxide (100 ppm), the bag was filled up with air packed in a compressed gas cylinder and allowed to stand in a thermostat at 40° C.

After 90 minutes, the Petri dish was taken out and the linoleic acid on the bottom face of the Petri dish was washed into a vial with the use of 2.5 mL of ethanol. 16 µL of this ethanol solution was weighed and 4 mL of 75% ethanol, 41 µL of a 30% aqueous ammonium thiocyanate solution and 41 µL of a 0.02 M iron (II) chloride solution in 3.5% hydrochloric acid were added thereto followed by thoroughly mixing. Exactly 3 minutes after adding the iron chloride solution, the absorbance at 500 nm (red color) was measured with an absorption spectrometer. As a control, the absorbance was measured with the use of nitrogen dioxide alone. As a blank, the absorbance was measured by adding neither nitrogen dioxide nor the removing agent according to the present invention (i.e., air alone). The change in the amount of the peroxide was evaluated in accordance with the following formula.

Inhibitory ratio (%) of peroxide formation=$[1-(A_2-A_0)/(A_1-A_0)]\times 100$ $A_0$: absorbance of blank
$A_1$: absorbance measured by using nitrogen dioxide alone
$A_2$: absorbance measured by adding removal agent of invention As a result, the inhibitory ratio of peroxide formation was 72%. This result indicates that the formation of linoleic acid peroxide was inhibited by adding the *Cryptomeria japonica* leaf essential oil headspace to nitrogen dioxide. Namely, this means that the *Cryptomeria japonica* leaf essential oil, i.e., the essential oil according to the present invention suppressed the oxidation ability of nitrogen dioxide.

Example 8

Test for Confirming Inhibition of Oxidation by Nitrogen Dioxide (2)

The oxidation inhibitory effect in the case of exposing the essential oil according to the present invention to nitrogen dioxide for 24 hours was examined in the following manner.

50 µL of the *Cryptomeria japonica* leaf essential oil was injected into a 1 L Tedlar bag which was then filled up with air packed in a compressed gas cylinder and allowed to stand in a thermostat at 40° C. for 10 minutes to give *Cryptomeria japonica* leaf essential oil headspace-containing Tedlar bag. 1 L of the *Cryptomeria japonica* leaf essential oil headspace was injected into a 10 L Tedlar bag. After adding 1350 mL of nitrogen dioxide (100 ppm), the bag was filled up with air packed in a compressed gas cylinder and allowed to stand in a thermostat at 40° C. for 24 hours.

Separately, a Petri dish uniformly coated with linoleic acid was prepared in the same manner as in Example 7 and put into a 10 L Tedlar bag, followed by heat-sealing the opening. To this Tedlar bag, each gas prepared 24 hours before use was injected and allowed to stand in a thermostat at 40° C. After 90 minutes, the Petri dish was taken out and treated as in the aforesaid test. The absorbances were measured at 500 nm (red color) and the change in the amount of the peroxide was evaluated in accordance with the formula of Example 7.

As a result, in the case of the gas prepared by mixing the essential oil according to the present invention with nitrogen dioxide and allowing to stand for 24 hours, the linoleic acid peroxide formation was inhibited at a ratio of 100%. Namely, this means that, 24 hours after mixing the essential oil according to the invention with nitrogen dioxide, the oxidation ability of nitrogen dioxide was completely suppressed.

Example 9

A harmful oxide-removing agent for spraying into space was prepared by blending 90 mass % of dipropylene glycol with 10 mass % of the *Cryptomeria japonica* leaf essential oil obtained in Example 1. The obtained harmful oxide-removing agent for spraying into space was sprayed into a space using an ultrasonic atomizer (manufactured by Echotech). As a result, formaldehyde and harmful oxides such as nitrogen oxides and sulfur oxides were removed thereby. In addition, this removing agent imparted a refreshing smell to the space.

Comparative Example 2

A harmful oxide-removing agent for spraying into space was prepared by blending 90 mass % of dipropylene glycol with 10 mass % of the *Cryptomeria japonica* leaf essential oil obtained in Comparative Example 1. The obtained harmful oxide-removing agent for spraying into space was sprayed into a space using an ultrasonic atomizer (manufactured by Echotech). As a result, formaldehyde and harmful oxides such as nitrogen oxides and sulfur oxides were removed thereby. However, a wood vinegar-like odor remained in the space after spraying.

Example 10

A harmful oxide-removing agent for spraying into space was prepared by blending 50 mass % of 3-methoxy-3-methyl-1-butanol with 50 mass % of the *Chamaecyparis obtusa Chamaecyparis* leaf essential oil obtained in Example 2. The obtained harmful oxide-removing agent was sprayed into a space using a heat transpiration device (deodorization plug manufactured by S.T.). As a result, formaldehyde and harmful oxides such as nitrogen oxides and sulfur oxides were removed thereby.

Comparative Example 3

A harmful oxide-removing agent for spraying into space was prepared by blending 50 mass % of 3-methoxy-3-methyl-1-butanol with 50 mass % of *Abies sachalinensis* leaf essential oil which was obtained in the same manner as in Comparative Example 1 except that *Abies sachalinensis* leaves were used as a substitute for the *Chamaecyparis obtusa Chamaecyparis* leaves. The obtained harmful oxide-removing agent was sprayed into a space using a heat transpiration device (deodorization plug manufactured by S.T.). As a result, formaldehyde and harmful oxides such as nitrogen oxides and sulfur oxides were removed thereby. However, a strong phenol-like odor remained in the space after spraying.

Example 11

A harmful oxide-removing agent for spraying into space was prepared by solubilizing 2 mass % of the *Chamaecyparis obtusa Chamaecyparis* leaf essential oil obtained in Example 3 in water with the use of 5 mass % of a surfactant (polyoxyethylene alkyl ether). This harmful oxide-removing agent was sprayed into a space using a marketed pump spray. As a result, formaldehyde and harmful oxides such as nitrogen oxides and sulfur oxides were removed thereby.

Example 12

A harmful oxide-removing agent for spraying into space was prepared by dispersing 0.1 mass % of the *Chamaecyparis obtusa Chamaecyparis* leaf essential oil obtained in Example 3 in 99.9 mass % of water. This harmful oxide-removing agent was sprayed into a space using an ultrasonic atomizer (manufactured by Echotech). As a result, formaldehyde and harmful oxides such as nitrogen oxides and sulfur oxides were removed thereby.

Example 13

A harmful oxide-removing agent for volatilizing into space was prepared by dispersing 3 g of κ-carrageenan, which was employed as a gelling agent, in a liquid mixture containing 3.0 g of the *Cryptomeria japonica* essential oil obtained in Example 1, 10 g of propylene glycol and 84 g of water, heating the dispersion at about 60° C., filling it in a top-opened cup type container and then solidifying therein by cooling. The obtained gel product was placed in a room, wherein an oil heater was used, and allowed to volatilize. Thus, formaldehyde and harmful oxides such as nitrogen oxides and sulfur oxides were removed thereby over about 1 month.

Example 14

Figure 2:
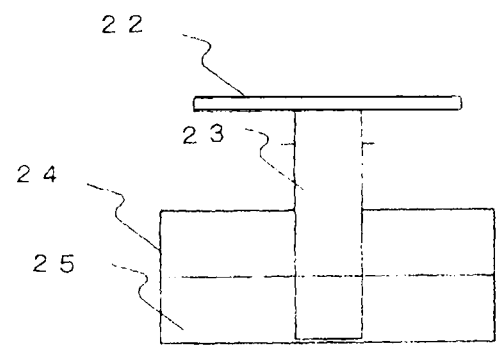
FIG. 2 is a drawing which shows a volatilization device used in Example 9.

A harmful oxide-removing agent for volatilizing into space was prepared by solubilizing 2 mass % of the *Abies sachalinensis* leaf essential oil obtained in Example 2 in water with the use of 5 mass % of a surfactant (polyoxyethylene alkyl ether). The obtained product was placed in a room, wherein an oil heater was used, by using the volatilization device as shown in FIG. 2 and allowed to volatilize. Thus, formaldehyde and harmful oxides such as nitrogen oxides and sulfur oxides were removed thereby over about 3 months.

Example 15

Figure 3:
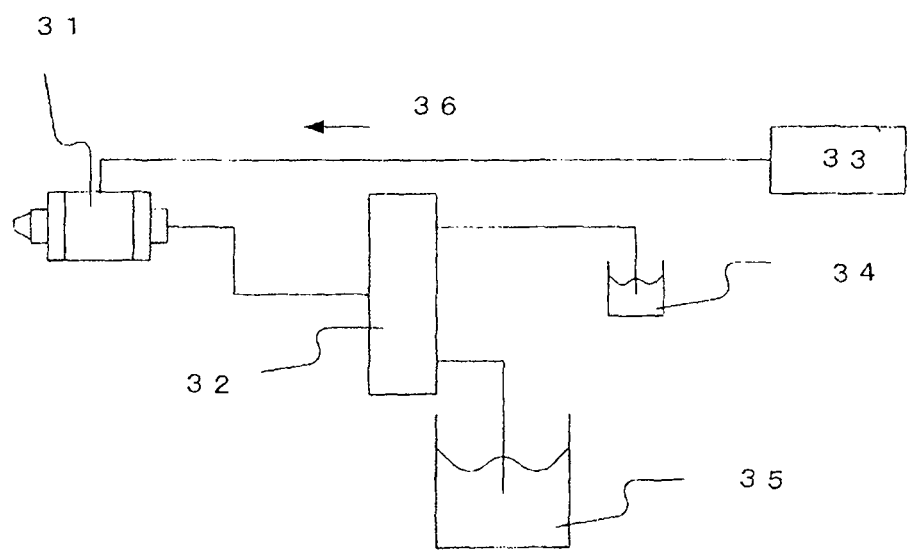
FIG. 3 is a diagram which shows a pressurized air atomization spraying device used in Example 10.

The *Chamaecyparis obtusa Chamaecyparis* essential oil obtained in Example 3 was sprayed at a rate of 5 mL/min into a room, wherein an oil heater was used, for 8 hours by using the pressurized air atomization spraying device as shown in FIG. 3. After 8 hours, the concentrations of formaldehyde and harmful oxides such as nitrogen oxides and sulfur oxides were lowered compared with the levels before using.

INDUSTRIAL APPLICABILITY

The monoterpene component-rich essential oil according to the present invention can be obtained from coniferous leaves. This essential oil is usable as an environmental pollutant-removing agent and as a starting material for the individual monoterpenes.

Therefore, the present invention is applicable in resource recycling and forest management as a technique for producing economically valuable substances from coniferous leaves which have been almost discarded hitherto.

DESCRIPTION OF REFERENCE NUMERALS

1: microwave distillation device
2: distillation tank
3: microwave heater
4: stirring blade
5: gas stream inlet tube
6: distillate outlet tube
7: condenser
8: heating controller
9: vacuum pump
10: pressure controlling valve
11: pressure controller
12: target material to be distilled
13: extract
21: volatilization device
22: volatilized matter
23: suction wick
24: container
25: removing agent
30: pressurized air atomization spraying device
31: gas/liquid mixing spray nozzle
32: 2-liquid flow rate-controller/feeder
33: compressor
34: essential oil
35: water
36: air

The invention claimed is:
1. A method for producing a monoterpene component-rich essential oil comprising 90% or more of at least one monoterpene component, the method comprising:
heating at least one coniferous leaf by irradiating with microwave at a reduced pressure of 20 to 80 kPa followed by distillation with water which is inherently contained in the leaf;
cooling volatile components; and
collecting an oily fraction thus obtained.

* * * * *